(12) United States Patent
Gilson et al.

(10) Patent No.: US 6,245,090 B1
(45) Date of Patent: *Jun. 12, 2001

(54) TRANSCATHETER OCCLUDING IMPLANT

(75) Inventors: Paul Gilson, Moycullen; Eamon Brady, Elphin, both of (IE)

(73) Assignee: Salviac Limited, Dublin (IE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/188,473

(22) Filed: Nov. 9, 1998

(30) Foreign Application Priority Data

Nov. 7, 1997 (IE) .................................. S970791

(51) Int. Cl.$^7$ .................................................. A61B 17/00
(52) U.S. Cl. ............................................................ 606/213
(58) Field of Search ................................ 606/213, 215, 606/151, 216–217, 153, 191, 198, 78; 604/167, 281; 600/32; 623/11, 1, 7, 8, 12, 16

(56) References Cited

U.S. PATENT DOCUMENTS

| | | |
|---|---|---|
| 4,365,621 | 12/1982 | Brundin . |
| 4,979,947 | 12/1990 | Berman . |
| 5,108,420 | 4/1992 | Marks ................................ 606/213 |
| 5,192,301 | 3/1993 | Kamiya et al. . |
| 5,634,936 | 6/1997 | Linden et al. . |
| 5,823,198 | 10/1998 | Jones et al. . |
| 5,824,081 | 10/1998 | Knapp et al. . |
| 5,853,422 | * 12/1998 | Huebsch et al. ..................... 606/213 |
| 5,876,452 | 3/1999 | Athanasiou et al. . |

FOREIGN PATENT DOCUMENTS

| | | |
|---|---|---|
| 0467516A1 | 1/1992 | (EP) . |
| 0547530A1 | 6/1993 | (EP) . |
| 2641692 | 7/1990 | (FR) . |
| WO 92/19162 | 11/1992 | (WO) . |
| WO 94/26175 | 11/1994 | (WO) . |
| WO 97/41778 | 11/1997 | (WO) . |
| PCT/IE98/00092 | 5/1999 | (WO) . |

OTHER PUBLICATIONS

Technical Encyclopedia ABC Chemie; vol. 2, p. 1240; Harry Deutch Publishing; 1979.

* cited by examiner

Primary Examiner—Michael Buiz
Assistant Examiner—Vikki Trinh
(74) Attorney, Agent, or Firm—Finnegan, Henderson, Farabow, Garrett & Dunner, L.L.P.

(57) ABSTRACT

A transcatheter occluding implant (50) is used to seal off a vessel lumen such as for arterial and venous embolization, cutting off of supply to tumors, male and female sterilization. There is illustrated a plug member of an open foam plastics material having good hysteresis properties in the form of a shaft 51 carrying annular supports. The implant (50) can be compressed into a very small size and then will expand to contact the internal bore of the vessel to form a force fit within the vessel lumen for secure anchoring of the implant. The open cell foam construction encourages tissue growth and thus further contributes to the stabilization of the implant.

39 Claims, 8 Drawing Sheets

TRANSCATHETER OCCLUDING IMPLANT

BACKGROUND OF THE INVENTION

1. Field of the Invention

The present invention relates to a transcatheter occluding implant for portion of a vessel lumen. Generally speaking, these implants comprise a plug for siting in the lumen and collapsible for transfer to its position in the lumen and include means for retaining the plug in the lumen.

There are numerous circumstances when there is a requirement to occlude a vessel in the treatment of medical conditions ranging from critical care applications to cosmetic applications. This invention relates to products for use in the occlusion of vessels in the human body.

2. Background Information

Conventionally vessels are occluded using coil devices. Coils are metallic based devices and typically consist of a metal wire wound into a helical spring. This length of spring however, has the property of being able to coil up into various pre-set shapes in order to occlude the vessel. Coils are used in a whole range of applications such as arterial and venous embolization, embolization of selective vessel supply to tumours, arterio-venous malformations, embolization of aneurysms and male sterilisation. Coils are unsuitable for closure of varicose veins, varicoceles and other similar venous applications due to the high level of collateral flow in the venous circulation.

A typical example of a device consisting of a wire for occluding an aperture within a body surface such as an arterial and ventricular septal defects is described in U.S. Pat. No. 5,108,420 (Marks).

Patent Ser. No. WO 92/19162 (Seld) shows a surgical implantation device to be placed within a patient's body and seal a herneal rupture in the abdominal fascia. Essentially, this consists of a annular support large enough to cover the opening and a plug which is placed through the opening. Similarly, patent Ser. No WO 97/41778 (Gilson) discloses a transcatheter occluder device which usually has a pair of spaced-apart annular supports interconnected by a narrow neck portion extending between the annular supports. The device is formed by a highly compressible foam plastics material and by virtue of its geometry, includes an opening, the neck siting in the defect opening while the annular supports remain on opposite sides of the opening. This device depends on its physical geometry for use in occlusion of holes. It is necessary that it engages and overlaps the side wall of the occlusion and is thus anchored by engagement with a peripheral face defining the opening.

Very often, vascular vessels need to be blocked. These vessels by the very nature of their anatomy can be described as lubricious tubes providing a very slippy environment and thus stabilising an occlusive device in such a vessel lumen can be extremely difficult. A further problem associated with such vessels is that they can have an indigenous pulse within the arterial wall. Such a pulse can be transmitted along the entire length of the vessel and against any occluding implant mounted therein. Further, by the very nature of the change in pressure within the vessel, the vessel, for example, will often expand and contract and there is thus a need for an implant that will be able to accommodate the changes in the bore of the vessel lumen in which it is placed.

OBJECTS

The present invention is directed towards providing an improved construction of transcatheter occluding implant.

In particular, the invention is directed towards the provision of an occluder that can be sited in vascular vessels.

Further, the invention is directed towards providing an improved construction of occluding implant that will accommodate the expansion and contraction of vessels in which it is sited.

SUMMARY OF THE INVENTION

According to the invention, there is provided a transcatheter occluding implant for portion of a vessel lumen comprising:

a plug member;

a lumen anchoring means including portion of an outer surface of the plug member for securing the plug member in the lumen;

expansion means for causing the lumen anchoring means to bear against the interior of the lumen;

self support means for retaining the anchoring means in position; and a resilient foam plastics material incorporated in the plug member forming at least portion of the plug member to provide the expansion means and the self supporting means.

A great advantage of using a resilient foam plastics material is that the plug member will expand and contract as required during use and thus will always accommodate, for example, pulsating flows of liquids and increases and decreases in liquid pressure, such as blood pressure.

Ideally, the portion of the outer surface forming the anchoring means provides a closed path around the plug member for total occlusion of the vessel on initial insertion and expansion. While it may not always be practical or necessary to block all the blood flow immediately, for example, where there would be an aneurysm and one would be relatively wary of rupturing the interior of the vessel lumen. In many other circumstances, it would not necessarily be a problem and obviously, where it is desired to cut off the flow, for example, of blood to a tumour, the quicker the blood flow can be stopped, the better.

Ideally, the outer surface of the plug member adjacent the interior of the lumen is of an open cell structure forming a plurality of tissue receiving orifices. The advantage of this is that as the plug member is retained in position, gradually tissue will be able to grow into the plug member so that the plug member will become a permanent fixture. For example, in many situations, it might not be desired to remove the implant, such as, for example, where it was used in the fallopian tube for the purpose of female sterilisation. Similarly, it might be extremely important when the implant was an aneurysm implant.

In a still further embodiment of the invention, all the plug member is of a foam plastics material.

Ideally, the foam plastics material is an open foam cell material. This is one of the best materials for using as it has extremely good hysteresis properties and, generally speaking, the foam plastics material should be manufactured from a polymeric material having good hysteresis properties.

Further, in accordance with the invention, the rate of expansion and compressibility of the foam material is chosen to be greater than that to which the bore of the lumen is subjected. It will be appreciated that if, for example, a vessel contracts and expands regularly, it is vital that the contraction and expansion of the implant does not cause abrasive damage to the vessel lumen.

Ideally, the surface area of the plug member in contact with the internal bore of the lumen on initial insertion exceeds the minimum area necessary to anchor the occluding implant within the lumen. While it would be possible to hold an implant in position by some fixing means, it is obviously much better that, from the start, the implant should hold itself in position.

Ideally the foam material has a pore size of less than 250 microns. Preferably the foam material has a pore size of less than 100 microns and may be within the range than 90% and in some instances greater than 94%.

One of the major advantages of the present invention is that the foam structure of the plug member is such as to confer a 3 dimensional structure to the implant. By virtue of an open cell foam construction, tissue growth can occur and following this, vascularisation of the implant. Following tissue growth, the presence of the tissue will promote the occlusion of the original implant which is now sustainable. The tissue growth occurs by virtue of the open cell nature of the foam structure. Thus, there may be situations where, for example, it is now possible, without causing damage to the vessel walls, to offer a complete barrier to the flow of liquid through the lumen on initial insertion and expansion of the implant within the lumen. However, initially the transcatheter occluding implant would block most of the flow and then, as tissue growth it promoted, the total flow will be blocked. It will be appreciated that this will not always be the situation and indeed in many instances, the transcatheter occluding implant according to the invention will on first insertion, act as a total barrier to the flow of liquid.

In one embodiment of the invention, the plug member is substantially cylindrical in shape and may have circumferentially arranged open slots or longitudinally arranged open slots. The great advantage of these slots is that they would allow the plug member to be compress to a very small size and thus be able to expand to a relatively large diameter.

Ideally, the cylindrical plug member is bent around itself to form shapes of differing geometries. Many shapes may be required, for example, where it may not be practical to oversize the occluder device and also where there may be different shapes of vessel requiring occlusion.

In one embodiment of the invention, the plug member is in the form of a shaft carrying a plurality of spaced-apart annular supports. This is bound to be a very efficient way of manufacturing the implant.

Ideally, the plug member is in the form of a central shaft carrying two end portions of gradually increasing cross section. Such a device does not cause undue pressure on the internal bore of the vessel lumen. Ideally, each end face of the plug member is of dished configuration. Again, this allows for increased compressibility.

In one embodiment of the invention, the plug member comprises a central shaft having at its distal end an enlarged head formed from a plurality of radially arranged flights tapering towards its extremity and a tail portion at its proximal end comprising a plurality of longitudinally spaced-apart flights projecting radially from the shaft and a circular annular support mounted on the shaft intermediate the tail and head portions. This has been found to be a very satisfactory way of manufacturing the occluder which is tightly anchored without causing damage to the vessel in which it is mounted.

When the implant is an aneurysm, it has a substantially spherical plug member. Very often, for an aneurysm, the plug member would be manufactured as to be slightly less in size than the aneurysm so as to ensure that undue pressure was not exerted on the vessel. In a situation such as this, the implant would probably be anchored relatively easily and because it would be in an aneurysm, it is unlikely to migrate.

Finally, the plug member includes attachment means for catheter placement and retrieval. Obviously, if the implant is to be sent and to be placed in position by a catheter, it is preferably that there often be some form of attachment means on the plug member to allow ease of manipulation and also particularly when it is desired possibly to remove the implant at some later stage.

BRIEF DESCRIPTION OF THE DRAWINGS

The invention will be more clearly understood from the following description thereof given by way of example only with reference to the accompanying drawings in which.

DESCRIPTION OF THE PREFERRED EMBODIMENTS

Figure 1:
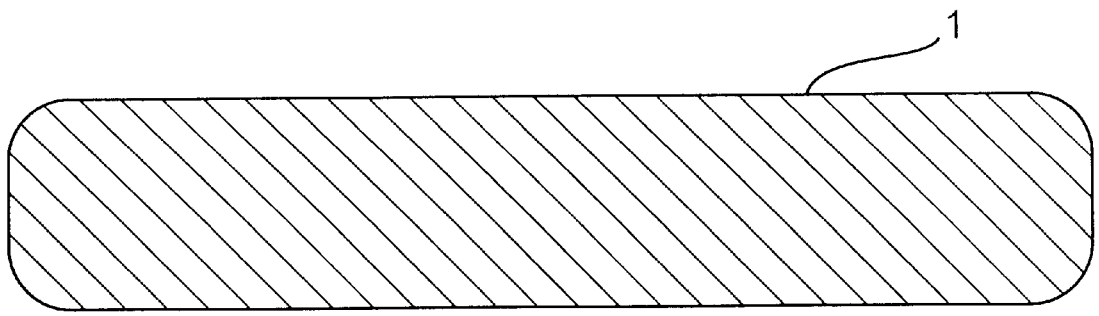
FIGS. 1 to 10 are cross-sectional views of various implants according to the invention.

Referring to the drawings, and initially to FIG. 1, there is illustrated a transcatheter occluding implant 1 for portion of a vessel lumen. The implant 1 comprises a deformable plug member which is formed from a resilient foam plastics material, in this embodiment, a polymeric material. It will be appreciated that when describing any of the foam plastics materials or any of the materials used in accordance with this invention, that they must all be essentially biologically compatible, or at least the outer surface.

Essentially, when delivered by a catheter 1 through a vessel lumen, it will obviously be compressed within the catheter and will then expand and must be self-supporting within the vessel into a configuration which will ensure that it is stabilised within the vessel by means of its geometry to form a force-fit within the lumen sufficient to anchor the implant 1 within the lumen. Accordingly, the implant 1 is designed so as to generate a frictional force within the vessel which exceeds the other forces acting on the implant. It is thus essentially a force fit within the lumen. Generally speaking, the plug member would expand normally to a configuration which is greater than at least part of the internal bore of the lumen to which it is being fitted. It is advantageous to consider these frictional forces in general terms.

This frictional force is the force stabilising the device in the vessel and is described by the equation $$Ff=\mu v. N \qquad \text{Eq. 1}$$

wherein Ff is the force of friction, $\mu v$ is the coefficient of friction and N is the normal force. The normal force N of the equation 1 is related to the pressure applied by the device to the vessel wall by the equation $$N=Pd. Ad \qquad \text{Eq. 2}$$

wherein Pd is the average pressure applied by the device on the vessel wall and Ad is the area of the device in contact with the vessel wall. The fluid pressure acting on the device generates a pressure force Fp defined by equation 3.

$$Fp=Pf(0.5. \pi \times r^2)=Pf.Av \qquad \text{Eq. 3}$$

Where Fp is the force acing on the device due to fluid pressure, Pf is the fluid pressure, r is the radius of the vessel and Av is the cross-sectional area of the vessel. Combining and rearranging equations 1, 2 and 3 leads to the concept of a critical area Ac, wherein the pressure force is exactly equal to the frictional force $$Ac=(\mu v. Pf. Av)/Pd \qquad \text{Eq. 4}$$

From equation 4 it is clear that the critical area is a function of four parameters the coefficient of friction between the device material and the vessel wall ($\mu v$)

the pressure applied by the fluid on the device (Pf)

the pressure applied by the device to the vessel wall (Pd) and the cross sectional area of the vessel (Av).

For the vessel stable implants according to this invention it is desirable that the area of the device in contact with the vessel wall be greater than the critical area. Ideally, the area of the device in contact with the vessel wall will be more than 50% greater than the critical area. The stability of the device can be accomplished by varying any of the above parameters to achieve the correct relationship between the critical area and the actual area of the device in contact with the vessel.

For a fully cylindrical device increasing the length of the device is the only method of increasing the critical area.

The coefficient of friction between the vessel and the device is typically between 0.01 and 0.25. The pressure applied to the device by fluid will vary between 0 and 200 mmHg. Thus, the pressure and area functions of the device need to be selected to match specific vessel applications.

The pressure applied by the device on the vessel wall can be increased by increasing the compressive modulus of the foam or by increasing the level of interference between the device and the vessel.

Figure 2:
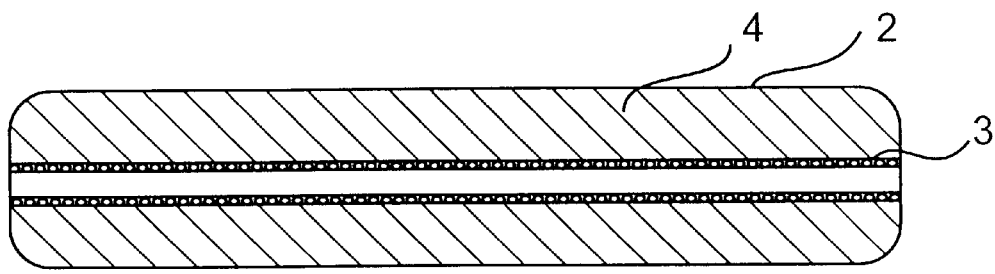

FIG. 2 shows an alternative construction of implant indicated generally by the reference numeral 2 which comprises a plug member having an inner sleeve 3 of a rigid polymeric material surrounded by a resilient foam plastics material 4. The sleeve 3 may be metallic.

Figure 3:
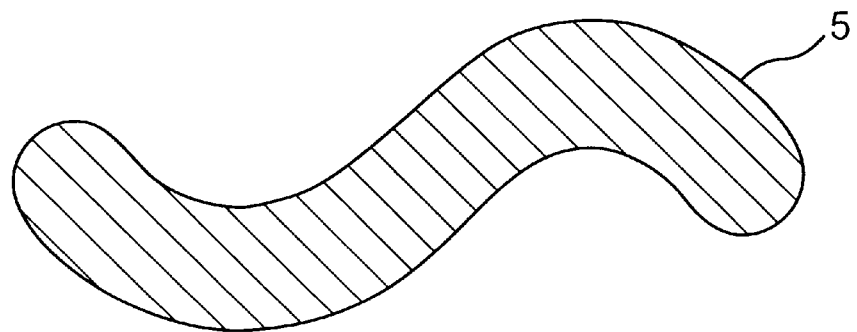
Figure 4:
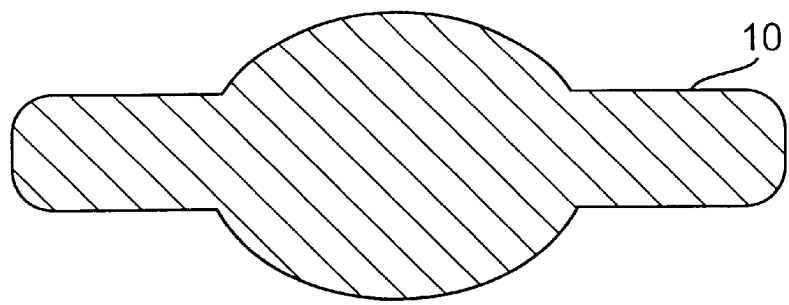

Referring now to FIG. 3, there is illustrated an implant indicated generally by the reference numeral 5 totally of a am plastics material in an S-shape which is a substantially cylindrical plug member bent around itself to form this shape.

Figure 5:
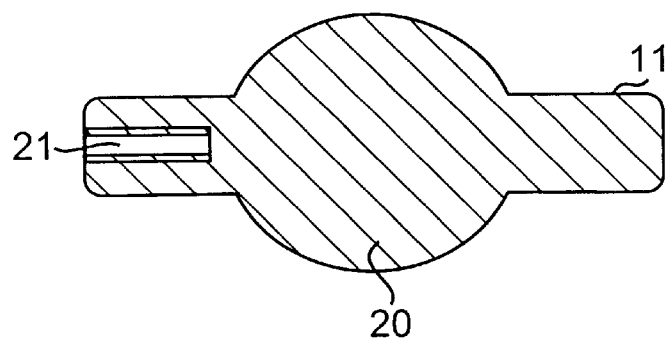
Figure 6:
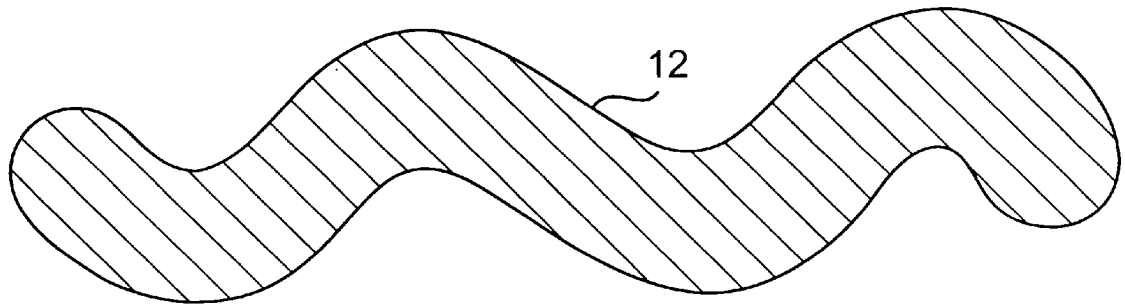
Figure 7:
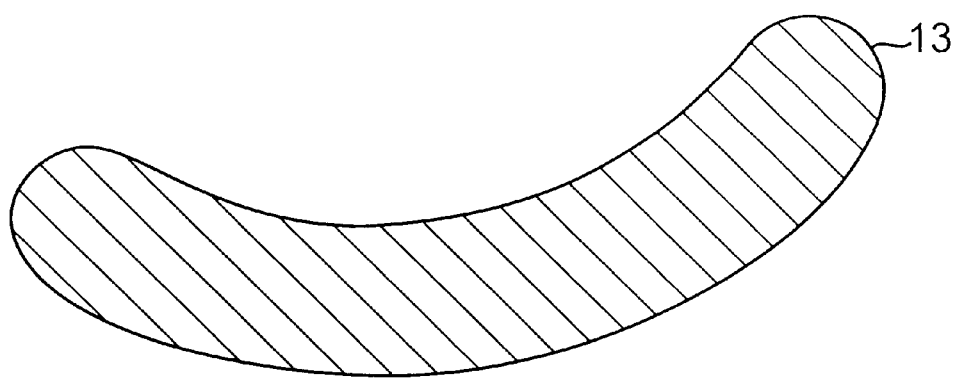
Figure 8:
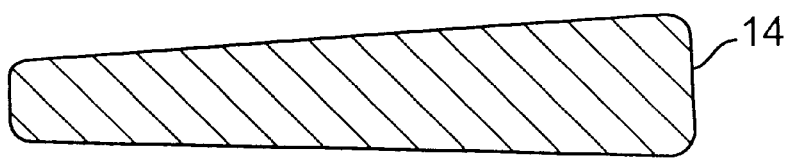

FIGS. 4 to 10 inclusive illustrate alternative constructions of implants indicated generally by the reference numerals 10, 11, 12, 13, 14, 15 and 16 respectively. These illustrate many different shapes of device. Referring specifically to FIG. 5, the implant 11 consists of a polymeric foam plug member 20 with an attachment mechanism 21. This attachment mechanism facilitates the gripping of the device by a gripping mechanism and facilitates re-positioning of the device or retrieval of the device. Attachment means can be achieved in a variety of ways and can be made suitable for virtually any geometry of device. The attachment means can for example be a threaded screw-in member or it may be a lock on gripper or other similar approaches may be used.

While a cylindrically shaped device is suitable for occluding vessels a series of other geometry's are also suitable. In many applications, it is desirable to have geometries which are substantially based on a cylindrical geometry but have material removed from the cylinder so as to facilitate delivery through a small diameter catheter. The device geometries described in FIGS. 1 and 2 have geometries wherein the central axis of the device is linear. Where it is not practical to over size the occluder device and where substantial amounts of material cannot be removed from the cross-section to aid delivery, then the geometry of the device needs to be such as to anchor itself in the vessel. This can be achieved by manufacturing a device wherein the central axis of the device is non-linear, and where the device has three dimensional curved surfaces. One such shape is an elongated "S" shaped device, the implant 5 of FIG. 3, or a spiral shaped device or a "C" shaped device such as the implants 11 and 13. These configurations have the advantage that the device wraps down in the catheter in an extended configuration. This reduces the device profile during delivery. Upon deployment the device shortens and expands. An additional benefit of these configurations is that the device can force the vessel to take up a non-linear configuration and this will stabilise the device without applying significant pressure to the vessel. There are many other geometry's which can be employed and the above are only representative examples.

In one embodiment the device is designed for the treatment of arterio-venous malformations (AVM's). AVM's are currently treated by cutting off the blood supply to the abnormal region. With this invention it is possible to cut off the blood supply by the use of a polymeric foam prosthesis placed proximal to the lesion. This foam device is sized so as to provide radial pressure on the artery. The foam structure will preferably be such as to promote tissue ingrowth and this will mechanically stabilise the device.

Figure 9:
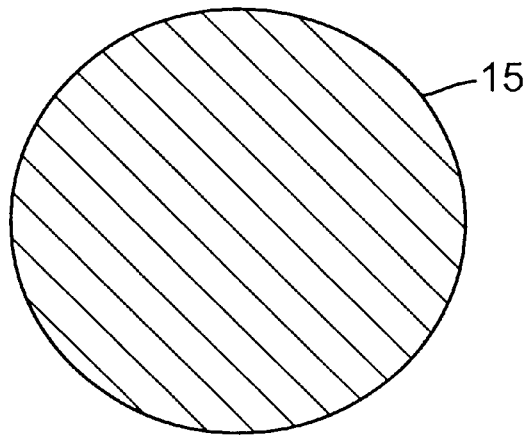
Figure 10:
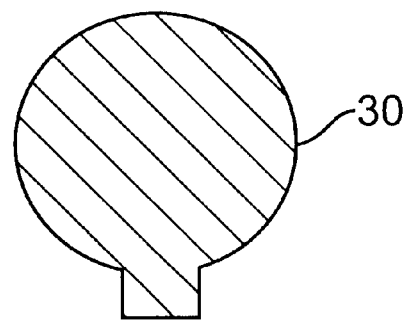
Figure 15:
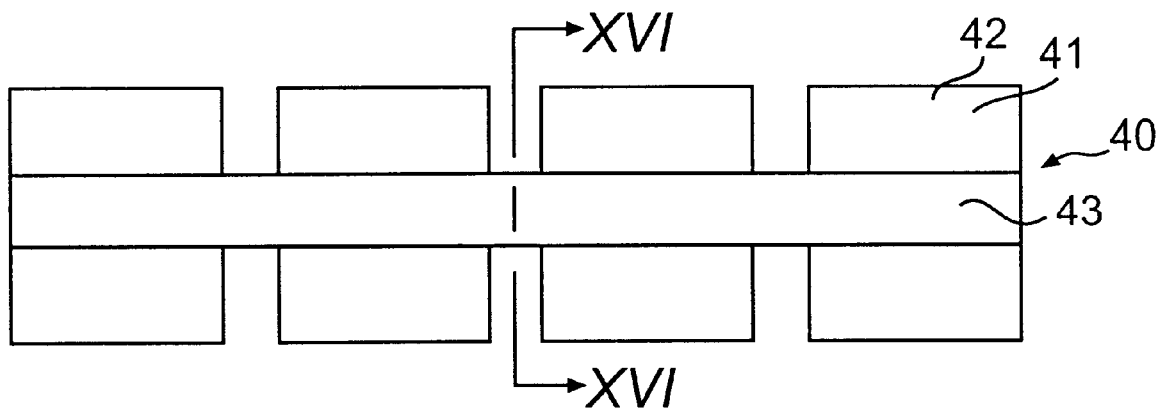
FIG. 15 is a plan view of still further implant according to the invention.

The implant 16 of FIG. 10 and 15 of FIG. 9 is designed to embolize a sac type aneurysm. In this embodiment the device is delivered to the aneurysm and deployed into the aneurysm. The geometry of the device is such that it fills completely the space in the aneurysm. This eliminates the need for significant levels of pressure or friction as the geometry of a berry type aneurysm will inherently stabilise any device which can comply with and substantially fill the aneurysm. The density of the foam for this type of application is ideally very low so as to apply minimal stress on the walls of the aneurysm. Densities of less than 100 kg/m³ are desirable. More ideally the foam density should be less than 40 kg/m³. Even more ideally the foam density should be less than 20 kg/m³. The pore structure of the foam should ideally be such as to promote tissue ingrowth. This will stabilise the device and remove residual pressure from the walls of the aneurysm. The foam should further be designed to be especially soft and deformable so as to avoid the application of additional pressure on the aneurysm wall. While in this specification, the concept of force fit is used, it must be appreciated that the force fit required is that required to ensure that the implant will remain in place and thus, for example, with the sack-type aneurysm, the amount of pressure or friction as it were that is required is relatively minimal. The implant will stay in position itself.

Figure 11:
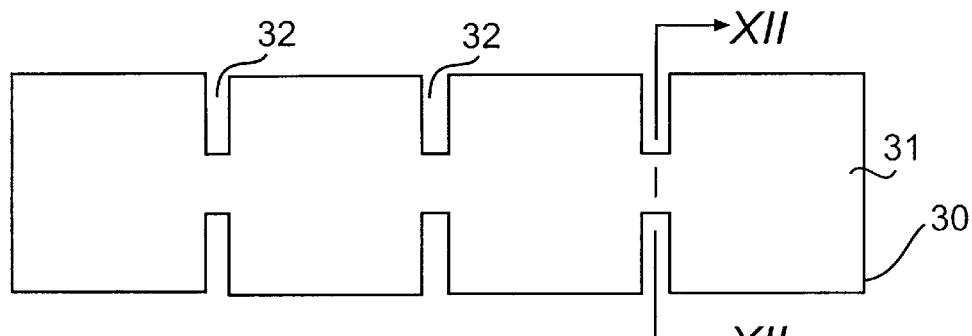
FIG. 11 is a plan view of another implant according to the invention.
Figure 12:
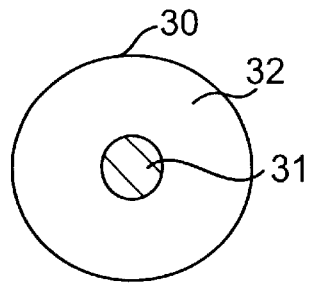
FIG. 12 is a cross sectional view in the direction of the arrows XII—XII of FIG. 11.

Referring now to FIGS. 11 and 12, there is illustrated an implant indicated generally by the reference numeral 30 having a plug member 31 which includes a plurality of circumferentially arranged open slots 32 which allow for compressibility and provide in effect deformation accommodating means.

Figure 13:
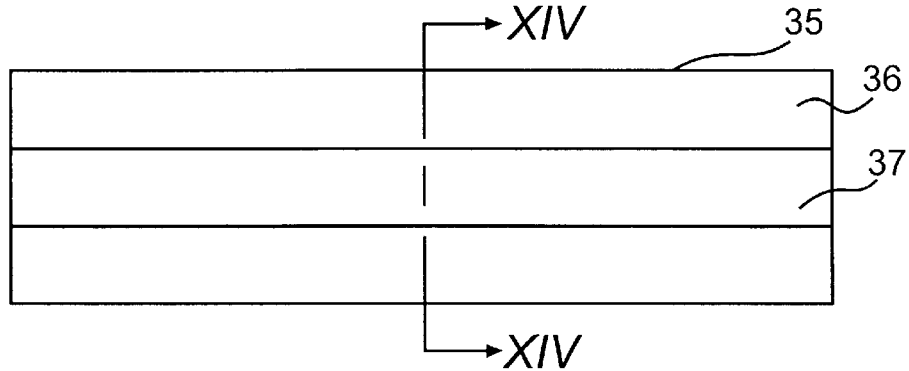
FIG. 13 is a plan view of still further implant according to the invention.
Figure 14:
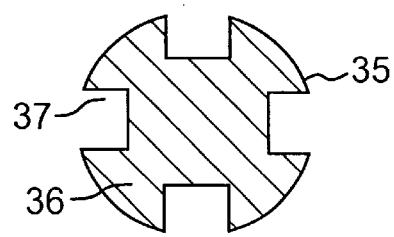
FIG. 14 is a cross sectional view in the direction of the arrows XIV—XIV of FIG. 13.

Referring now to FIGS. 12 and 13, there is illustrated an alternative implant indicated generally by the reference numeral 35 having a plug member 36 and a plurality of longitudinally arranged open slots 37 again forming deformation accommodating means.

Figure 16:
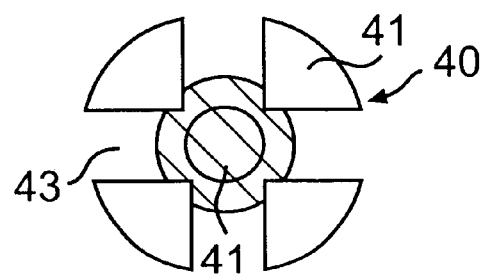
FIG. 16 is a sectional view in the direction of the arrows XVI—XVI of FIG. 15.

Referring now to FIGS. 15 and 16, there is illustrated a still further implant indicated generally by the reference numeral 40 again having a plug member 41 of a substantially cylindrical shape. In this embodiment, there is provided circumferentially arranged open slots 42 and longitudinally arranged open slots 43. Again, this will provide greater flexure and will allow for the deformation of the implant 40.

Figure 19:
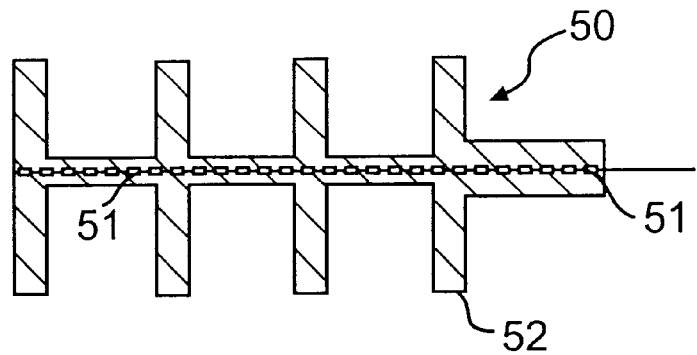
FIG. 19 is a sectional view in the direction of the arrows XIX—XIX of FIG. 18.
Figure 18:
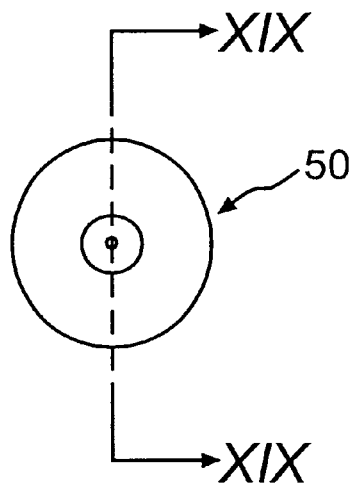
FIG. 18 is an end view of the implant.
Figure 17:
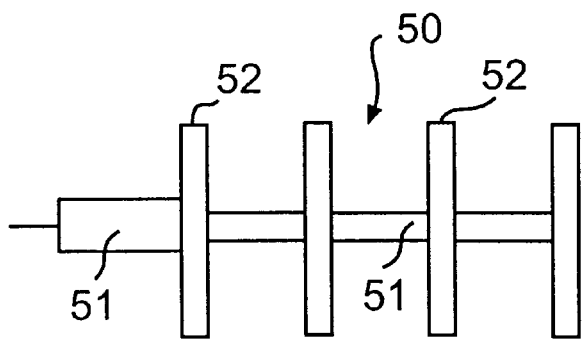
FIG. 17 is a plan view of another implant according to the invention.

Referring now to FIGS. 17 to 19 inclusive, there is illustrated an implant indicated generally by the reference numeral 50 having a plug member in the form of a shaft 51 carrying a plurality of spaced-apart annular supports 52. Again, the annular supports will form deformation accommodating means and will provide adequate barriers to the fluid while allowing for ease of deployment.

Figure 22:
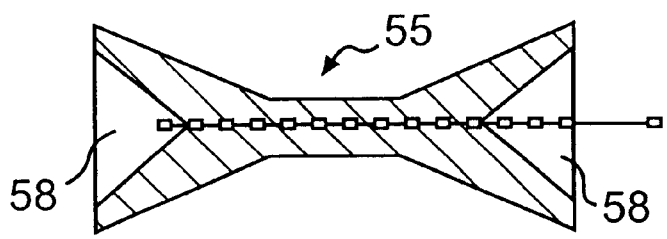
FIG. 22 is a sectional view in the direction of the arrows XXII—XXII of FIG. 21.
Figure 21:
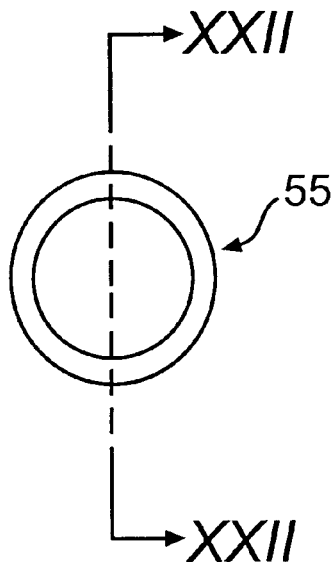
FIG. 21 is an end view of the implant of FIG. 20.
Figure 20:
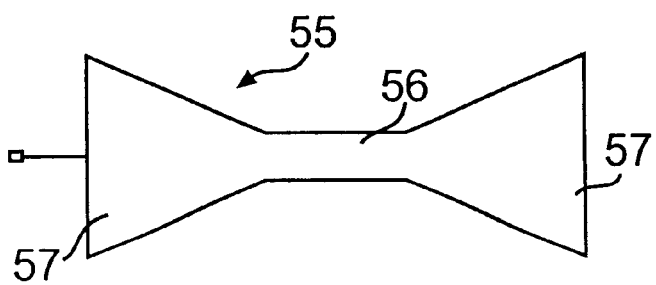
FIG. 20 is a plan view of a still further implant according to the invention.

Referring to FIGS. 20 to 22 inclusive, there is illustrated an implant indicated generally by the reference numeral 55 in the form of a central shaft 56 having end portions 57 of gradually increasing cross section, each having an end face 58 of dished construction. Again, this will assist deployment.

Figure 25:
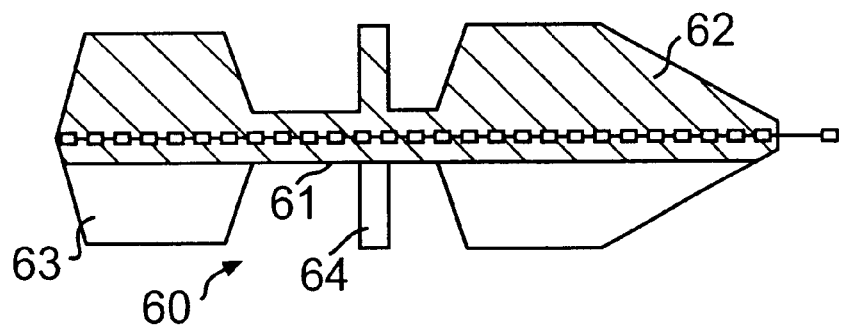
FIG. 25 is a sectional view in the direction of the arrows XXV—XXV of FIG. 24.
Figure 24:
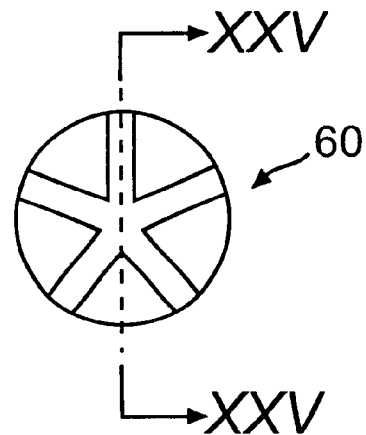
FIG. 24 is an end view of the implant of FIG. 23.
Figure 23:
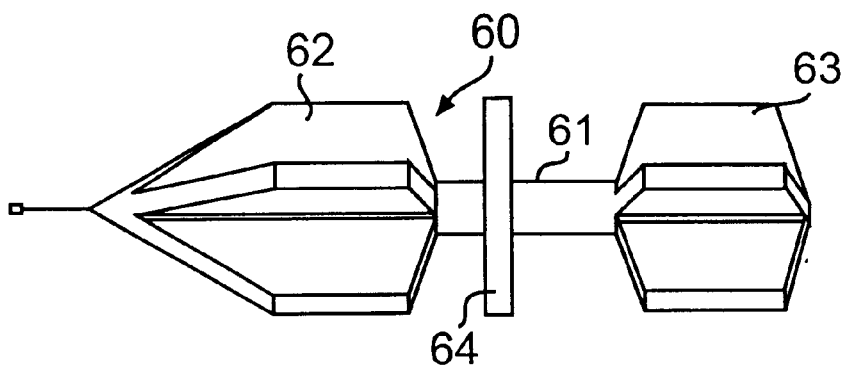
FIG. 23 is a plan view of a still further implant according to the invention.

Referring now to FIGS. 23 to 25, there is illustrated an implant indicated generally by the reference numeral 60 having a plug member formed from a central shaft 61 having an enlarged head at its distal end formed from a plurality of radially arranged tapering flights 62 and a tail portion at its proximal end comprising a plurality of longitudinally arranged spaced-apart flights 63. A central circular annular support 64 is mounted on the shift 61. This has been found to be a particularly useful construction. The flights will allow the securement of the implant within the vessel, while at the same time maximum flexibility is provided.

When, for example, the implant is designed to occlude the fallopian tube for the purpose of female sterilisation, the device geometry is such that when released from the catheter that it expands to fully occlude the vessel. There are various geometry's which could be used for this application. An important feature is the ability of the implant to expand to a size equal to or greater than that of the vessel. This generates compressive interference with the wall of the tube and holds the implant in place.

In yet another use of the implants of this invention, the implant is designed for the purpose of embolising selective vessel supply to tumours. In this embodiment the implant geometry is such that when released from the catheter it expands to fully occlude the vessel. There are various geometry's which could be used for this application. An important feature of this embodiment is the ability of the implant to expand to a size equal to or greater than that of the vessel. This generates compressive interference with the wall of the tube and holds the implant in place.

In yet another embodiment of this invention, the implant may be designed for the purpose of embolising varicose veins. In this embodiment, the implant occludes the varicose vein over a substantial portion of its length. There are various geometries which could be used for this application. Several implant type devices could be deployed along the vessel independently so as to occlude the vessel on a segmental basis. Alternatively, the implant could consist of a segmented design wherein occluding segments are attached together by a common core or the implant could be designed with a high length to diameter ratio so as to occlude the vessel completely over its entire length.

It will be obvious from the above that the geometry of the implant will be chosen so as to deform the implant compressively or to otherwise deform it so as to secure the implant at the occlusion site. Suitable geometries are numerous but are not limited to the following 3-dimensional shapes.

Devices wherein the cross-sectional shape perpendicular to the vessel axis is a triangle, a rectangle, a polygon, an ellipse, an S-shaped surface, a C-shaped surface, or a surface compounded of portions of these shapes and wherein the cross-sectional shape parallel to the axis is a triangle, a rectangle, a polygon, an ellipse, an S-shaped surface, a C-shaped surface, or a surface compounded of portions of these shapes.

Devices wherein the geometry is constructed of a rod of various possible cross-sectional shapes such as triangular, rectangular, polygon, elliptical, S-shaped, C-shaped, or a shape compound of portions of these shapes, wherein the rod is shaped into a series secondary three dimensional configurations exemplary examples of which include but are not limited to a helical wound device, spiral wound device, a ball shaped coil device, a multilayer ball shaped coil device, a multilayer layer helical wound device and such like.

It is further envisaged that the implants according to the present invention will incorporate, as part of the plug member, a solid polymeric or metallic core to improve visualization or to provide some form of attachment means to assist in the delivery of the device and in certain circumstances, in its retrieval. The plug member could have a solid core member which could, for example, be a helically wound coil, a solid tube, a mandrel or any suitable construction only some of which have been illustrated.

Many plastics foam materials may be used in accordance with this invention such as those described in our copending patent applications. An open foam plastics material is particularly advantageous and ideally the outer surface of the plug member adjacent the interior of the lumen is of an open cell structure. The open cell structure will form a plurality of tissue receiving orifices and thus the implant can be in many instances totally incorporated into the patient's body. The pore size of the polymeric material will be selected to promote tissue growth and angiogenesis. Ideally, the pore size is less than 250 or 100 microns and may be as low as 30 to 50 microns. Again, the pore size will be chosen, depending on the requirement. Similarly, an optimal void content will depend on the implant geometry and the location of it. It has been found that in general a void content in excess of 80% is desirable. In some applications, the void content may exceed 90% or even be in excess of 94%, thus the foam material is essentially very flexible and of extremely low density so as to have good hysteresis properties.

Ideally, the foam material when used in a vessel which is continually expanding and contracting should be capable of expanding and contracting faster than the vessel so as not to put any undue strain on the vessel walls or to tend to separate from the vessel wall when the vessel wall expands.

As stated above, many polymeric materials may be used and it will be appreciated that as long as the implant or at least the outer surface of the implant is coated in a biologically compatible material, that any suitable materials may be used. It is envisaged that the porous polymeric material could be any polymer constructed from some or all of ether, ester, carbonate, urethane, urea, biuret, allophanate and siloxane.

Many polyurethanes are suitable such as a polyether urethane, a polyether urethane urea, a polyether carbonate urethane, a polyether carbonate urethane urea, a polycarbonate urethane, a polycarbonate urethane urea, a polycarbonate silicone urethane, a polycarbonate silicone urethane urea, a polydimethylsiloxane urethane, a polydimethylsiloxane urethane urea, a polyester urethane, a polyester urethane urea or mixture of these.

The porous polymeric member may be made from a silicone based polymer, a fluoropolymer, an olefin or a polyester.

Exemplary processes for the manufacture of devices of this invention include but are not limited to:

Injection blow moulding wherein material is injected into a mould in a liquid state and foams in the mould due to the expansion of a gas generated by either physical or chemical means.

Extrusion blow forming wherein liquid polymer is extruded from a high pressure die and foams due to the expansion of a gas by either physical or chemical means.

Extrusion blow forming wherein liquid polymer is extruded from a chemical means.

Phase inversion processes wherein a porous foam is generated from a polymer solution by bringing the polymer out of solution by the use of a non-solvent or thermally.

Lost core processes wherein porous foam is made by mixing a lost core material with the fluidised polymer, solidifying the polymer and subsequently removing the lost core material typically by a solution process.

Reaction blow moulding wherein a polymeric foam structure is generated by the simultaneous polymer chain extension and blowing processes, the blowing process may be due to either a condensation reaction associated with the formation of a supermolecular structure or due to the bolding of volatile solvents or due to the inclusion of a thermally degrading gas evolving compound or due to the solubilisation and expansion of dissolved or compressed gas in one or more of the reaction components.

Machining of a solid material into appropriately shaped porous structures may be either by mechanical machining or laser machining or chemical ablation.

Combinations of the above process may be used either to manufacture the device or to achieve a density sufficiently low for successful use.

The invention is not limited to the embodiments hereinbefore described which may be varied in construction and detail.

What is claimed is:

1. A transcatheter occluding implant for occluding a vessel lumen, comprising:
    a plug member having a porous outer surface, a compressed configuration allowing for transcatheter delivery to a vessel lumen to be occluded, and an expanded, occluding configuration;
    the plug member further including a lumen anchoring portion having a transverse dimension in the expanded configuration which is greater than a transverse dimension of at least a portion of an internal bore of the lumen in which it is to be deployed, the lumen anchoring portion providing a force fit within the lumen to secure the plug therein;
    the plug member being formed at least partially of a resilient foam plastics material, the resilient foam plastics material:
        assisting in causing the lumen anchoring portion to bear against the internal bore of the lumen when in the expanded configuration, providing support for retaining the anchoring portion in position in the lumen, and having a void content of greater than 70%.

2. A transcatheter occluding implant of claim 1 in which the outer surface of the plug member forms a part of the anchoring portion and provides a closed path around the plug member for total occlusion of the vessel on initial insertion and expansion.

3. A transcatheter occluding implant of claim 1, in which the outer surface of the plug member adjacent the interior of the lumen is of an open cell structure forming a plurality of tissue receiving orifices.

4. A transcatheter occluding implant of claim 1, in which substantially all the plug member is of a foam plastics material.

5. A transcatheter occluding implant of claim 1, in which the foam plastics material is an open foam cell material with good hysteresis properties.

6. A transcatheter occluding implant of claim 1, in which the foam plastics material is manufactured from a polymeric material having good hysteresis properties and in which the rate of expansion and compressibility of the foam material is chosen to be greater than that to which the bore of the lumen is subjected.

7. A transcatheter occluding implant of claim 1, in which the foam material has a pore size of less than 250 microns.

8. A transcatheter occluding implant of claim 1, in which the foam material has a pore size of less than 100 microns.

9. A transcatheter occluding implant of claim 1, in which the foam material has a pore size within the range of 30 to 50 microns.

10. A transcatheter occluding implant of claim 1, in which the foam material has a void content greater than 90%.

11. A transcatheter occluding implant of claim 1, in which the foam material has a void content greater than 94%.

12. A transcatheter occluding implant of claim 1, in which the surface area of the plug member in contact with the internal bore of the lumen on initial insertion exceeds the minimum area necessary to anchor the occluding implant within the lumen.

13. A transcatheter occluding implant of claim 1, in which the plug member is substantially cylindrical in shape.

14. A transcatheter occluding implant of claim 1, in which the plug member has a circumferentially arranged open slot.

15. A transcatheter occluding implant of claim 1, in which the plug member has a longitudinally arranged open slot.

16. A transcatheter occluding implant of claim 1 in which the plug member is substantially cylindrical in shape and in which the cylindrical plug member is bent around itself to form shapes of differing geometries.

17. A transcatheter occluding implant of claim 1 in which the plug member is in the form of a shaft carrying a plurality of spaced-apart annular supports.

18. A transcatheter occluding implant of claim 1, in which the plug member is in the form of a central shaft carrying two end portions of gradually increasing cross section and in which each end face of the plug member is of a dished configuration.

19. A transcatheter occluding implant of claim 1 in which the plug member comprises a central shaft having at its distal end an enlarged head formed from a plurality of radially arranged flights tapering towards its extremity and a tail portion at its proximal end comprising a plurality of longitudinally spaced-apart flights projecting radially from the shaft and a circular annular support mounted on the shaft intermediate the tail and head portions.

20. A transcatheter occluding implant of claim 1, in which the implant is an aneurysm implant having a substantially spherical plug member.

21. A transcatheter occluding implant for occluding a vessel lumen, comprising:
   a plug member having a porous outer surface, a compressed configuration allowing for transcatheter delivery to a vessel lumen to be occluded, and an expanded, occluding configuration;
   the plug member further including a lumen anchoring portion having a transverse dimension in the expanded configuration which is greater than a transverse dimension of at least a portion of an internal bore of the lumen in which it is to be deployed, the lumen anchoring portion providing a force fit within the lumen to secure the plug therein; and
   an attachment mechanism formed in the plug member for allowing repositioning and removal of the plug member with respect to the vessel lumen;
   the plug member being formed at least partially of a resilient foam plastics material, the resilient foam plastics material:
      assisting in causing the lumen anchoring portion to bear against the internal bore of the lumen when in the expanded configuration, providing support for retaining the anchoring portion in position in the lumen, and having a void content of greater than 70%.

22. A transcatheter occluding implant of claim 21, wherein the attachment mechanism includes an opening extending along a longitudinal axis of the plug member.

23. A transcatheter occluding implant of claim 21, in which the outer surface of the plug member adjacent the interior of the lumen is of an open cell structure forming a plurality of tissue receiving orifices.

24. A transcatheter occluding implant of claim 21, in which substantially all the plug member is of a foam plastics material.

25. A transcatheter occluding implant of claim 21, in which the foam material has a pore size of less than 250 microns.

26. A transcatheter occluding implant of claim 21, in which the foam material has a pore size of less than 100 microns.

27. A transcatheter occluding implant of claim 21, in which the foam material has a pore size within the range of 30 to 50 microns.

28. A transcatheter occluding implant of claim 21, in which the foam material has a void content of greater than 70%.

29. A transcatheter occluding implant of claim 21, in which the foam material has a void content greater than 90%.

30. A transcatheter occluding implant of claim 21, in which the foam material has a void content greater than 94%.

31. A transcatheter occluding implant of claim 21, in which the surface area of the plug member in contact with the internal bore of the lumen on initial insertion exceeds the minimum area necessary to anchor the occluding implant within the lumen.

32. A transcatheter occluding implant of claim 21, in which the plug member is substantially cylindrical in shape.

33. A transcatheter occluding implant of claim 21, in which the plug member has a circumferentially arranged open slot.

34. A transcatheter occluding implant of claim 21, in which the plug member has a longitudinally arranged open slot.

35. A transcatheter occluding implant of claim 21, in which the plug member is substantially cylindrical in shape and in which the cylindrical plug member is bent around itself to form shapes of differing geometries.

36. A transcatheter occluding implant of claim 21, in which the plug member is in the form of a shaft carrying a plurality of spaced-apart annular supports.

37. A transcatheter occluding implant of claim 21, in which the plug member is in the form of a central shaft carrying two end portions of gradually increasing cross section and in which each end face of the plug member is of a dished configuration.

38. A transcatheter occluding implant of claim 21, in which the plug member comprises a central shaft having at its distal end an enlarged head formed from a plurality of radially arranged flights tapering towards its extremity and a tail portion at its proximal end comprising a plurality of longitudinally spaced-apart flights projecting radially from the shaft and a circular annular support mounted on the shaft intermediate the tail and head portions.

39. A transcatheter occluding implant of claim 21, in which the implant is an aneurysm implant having a substantially spherical plug member.

* * * * *